United States Patent
Kim et al.

(10) Patent No.: US 9,530,205 B2
(45) Date of Patent: Dec. 27, 2016

(54) POLYP DETECTION APPARATUS AND METHOD OF OPERATING THE SAME

(71) Applicants: SAMSUNG ELECTRONICS CO., LTD., Suwon-si (KR); GWANGJU INSTITUTE OF SCIENCE AND TECHNOLOGY, Gwangju (KR)

(72) Inventors: Sung-hyun Kim, Yongin-si (KR); Kuk-jin Yoon, Gwangju (KR); Seung-hwan Bae, Gwangju (KR); Yeong-jun Jo, Gwangju (KR); Tae-kyung Kim, Seongnam-si (KR); Ji-woon Jung, Yongin-si (KR)

(73) Assignees: SAMSUNG ELECTRONICS CO., LTD., Suwon-si (KR); GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 122 days.

(21) Appl. No.: 14/479,534

(22) Filed: Sep. 8, 2014

(65) Prior Publication Data
US 2015/0117729 A1    Apr. 30, 2015

(30) Foreign Application Priority Data
Oct. 30, 2013    (KR) .................. 10-2013-0130334

(51) Int. Cl.
*G06T 7/00* (2006.01)
*A61B 1/00* (2006.01)
*G06K 9/34* (2006.01)

(52) U.S. Cl.
CPC ......... *G06T 7/0012* (2013.01); *A61B 1/00009* (2013.01); *G06K 9/346* (2013.01); *G06T 2207/10068* (2013.01); *G06T 2207/30032* (2013.01)

(58) Field of Classification Search
USPC .................................. 382/283, 190
See application file for complete search history.

(56) References Cited

U.S. PATENT DOCUMENTS

| 2008/0058593 | A1 | 3/2008 | Gu et al. | |
| 2009/0073257 | A1* | 3/2009 | Tanaka | G06T 17/00 348/45 |
| 2009/0074268 | A1* | 3/2009 | Tanaka | G06T 7/0012 382/128 |
| 2011/0176710 | A1* | 7/2011 | Mattiuzzi | G06F 19/321 382/128 |

(Continued)

OTHER PUBLICATIONS

Oh, JungHwan, et al. "Informative frame classification for endoscopy video." Medical Image Analysis 11.2 (2007): 110-127.*

(Continued)

*Primary Examiner* — Bhavesh Mehta
*Assistant Examiner* — Narek Zohrabyan
(74) *Attorney, Agent, or Firm* — Sughrue Mion, PLLC (57) ABSTRACT

A polyp detection apparatus and a method of operating the same are provided. The method of operating a polyp detection apparatus includes: generating an image of an object; detecting a polyp candidate region based on the generated image; detecting a reflected light region within the detected polyp candidate region; and displaying a final polyp region by excluding the detected reflected light region from the polyp candidate region.

21 Claims, 10 Drawing Sheets

(56) References Cited

U.S. PATENT DOCUMENTS

2011/0301447 A1* 12/2011 Park .................. G06T 7/0016
  600/407
2014/0092226 A1* 4/2014 Kuriyama .......... G02B 23/2469
  348/68

OTHER PUBLICATIONS

Park, Sun Young, et al. "A colon video analysis framework for polyp detection." IEEE Transactions on Biomedical Engineering 59.5 (2012): 1408-1418.*

Bernal, Jorge, Javier Sánchez, and Fernando Vilarino. "Impact of image preprocessing methods on polyp localization in colonoscopy frames." 2013 35th Annual International Conference of the IEEE Engineering in Medicine and Biology Society (EMBC). IEEE, 2013.*

Bernal, Jorge, Javier Sánchez, and Fernando Vilarino. "Towards automatic polyp detection with a polyp appearance model." Pattern Recognition 45.9 (2012): 3166-3182.*

Lieberman, M.D., et al., "Use of Colonoscopy to Screen Asymptomatic Adults for Colorectal Cancer", The New England Journal of Medicine, Jul. 20, 2000, vol. 343, No. 3, pp. 162-168.

Criminisi, A., et al., "Object Removal by Exemplar-Based Inpainting", Computer Vision and Pattern Recognition, 2003. Proceedings. 2003 IEEE Computer Society Conference on. vol. 2. 8 pages.

Arnold, Mirko, et al., "Automatic Segmentation and Inpainting of Specular Highlights for Endoscopic Imaging", EURASIP Journal on Image and Video Processing, vol. 2010, Dec. 2, 2010, Article ID 814319, 12 pages.

* cited by examiner

POLYP DETECTION APPARATUS AND METHOD OF OPERATING THE SAME

CROSS-REFERENCE TO RELATED APPLICATIONS

This application claims the benefit of Korean Patent Application No. 10-2013-0130334, filed on Oct. 30, 2013, in the Korean Intellectual Property Office, the disclosure of which is incorporated herein in its entirety by reference.

BACKGROUND

1. Field

One or more exemplary embodiments relate to a polyp detection apparatus and a method of operating the same, and more particularly, to a polyp detection apparatus capable of detecting a polyp region based on an image acquired by using an endoscope and a method of operating the same.

2. Description of the Related Art

An endoscope is a medical instrument that is inserted into a human body in order to visually inspect organs and body cavities of the human body which cannot otherwise be seen without performing a surgical procedure on or making large incisions in the human body. During the early stage of development, endoscopes were simply used to observe organs or body cavities by inserting a thin and long insertion portion into the human body.

Since then, with the development of image processing technologies, black and white cameras have been introduced to observe in detail lesions in various body cavities. More recently, the simple black and white cameras have been replaced with color cameras with high resolution, which enable more precise examination of lesions and body organs. Furthermore, a new medical procedure referred to as chromoendoscopy has been developed to image the surface of a body cavity by dying the surface by using a particular colorant according to lesions to be distinguished.

Risks associated with gastric cancers and colorectal cancers may be reduced by detecting polyps from an image acquired by using an endoscope and removing or treating the detected polyps at an early stage.

SUMMARY

One or more exemplary embodiments include a polyp detection apparatus that acquires an image of an object by using an endoscope and excludes reflected light regions from detected polyp candidate regions based on the acquired image and a method of operating the same.

Additional aspects will be set forth in part in the description which follows and, in part, will be apparent from the description, or may be learned by practice of the presented exemplary embodiments.

According to an aspect of an exemplary embodiment, there is provided a method of operating a polyp detection apparatus, the method including: generating an image of an object; detecting a polyp candidate region based on the generated image; detecting a reflected light region within the detected polyp candidate region; and displaying a final polyp region by excluding the detected reflected light region from the polyp candidate region.

The detecting of the polyp candidate region may be performed based on feature information of polyps.

The method may further include converting the generated image into a binary image, wherein the detecting of the reflected light region is performed based on the binary image.

The detecting of the reflected light region may be performed based on a number of pixels of the polyp candidate region and a number of estimated reflected light regions.

The detecting of the reflected light region may be performed based on an area of the polyp candidate region and an area of an estimated reflected light region.

The detecting of the reflected light region may include selectively performing a first stage and a second stage, wherein the first stage includes comparing a first value with a first reference value, the first value being obtained by dividing a number of pixels of an estimated reflected light region included in the polyp candidate region by a number of pixels of the polyp candidate region, with a first reference value, and the second stage includes comparing a second value with a second reference value, the second value being obtained by dividing an area of the estimated reflected light region included in the polyp candidate region by an area of the polyp candidate region, with a second reference value.

The detecting of the reflected light region includes performing the second stage when the value is greater than the first reference value in the first stage.

The detecting of the reflected light region includes determining the estimated reflected light region to be the final polyp region, if the first value is equal to or less than the first reference value in the first stage.

The detecting of the reflected light region includes determining the estimated reflected light region to be the reflected light region if the second value is greater than the second reference value in the second stage.

The detecting of the reflected light region includes determining the estimated reflected light region to be the final polyp region, if the second value is equal to or less than the second reference value in the second stage.

The method may further include comparing the final polyp region with a previously detected polyp region, wherein the displaying of the final polyp region includes displaying a movement trace of the final polyp region when the final polyp region is the same as the previously detected polyp region.

According to another aspect of an exemplary embodiment, there is provided a polyp detection apparatus including: an imager configured to image an object and thereby generate an image signal; an image generator configured to generate an image based on the image signal received from the imager; a polyp candidate region detector configured to detect a polyp candidate region based on the generated image; a reflected light region detector configured to detect a reflected light region within the detected polyp candidate region; and a display configured to display a final polyp region by excluding the detected reflected light region from the polyp candidate region.

The polyp candidate region detector may be configured to detect the polyp candidate region based on feature information of polyps.

The reflected light region detector may be configured to convert the generated image into a binary image and detect the reflected light region based on the binary image.

The reflected light region detector may be configured to detect the reflected light region based on a number of pixels of the polyp candidate region and a number of estimated reflected light regions.

The reflected light region detector may be configured to detect the reflected light region based on an area of the polyp candidate region and an area of an estimated reflected light region.

The reflected light region detector may be configured to compare a first value with a first reference value, the first value being obtained by dividing a number of pixels of an estimated reflected light region included in the polyp candidate region by a number of pixels of the polyp candidate region, and compare a second value with a second reference value, the second value being obtained by dividing an area of the estimated reflected light region included in the polyp candidate region by an area of the polyp candidate region.

The reflected light region detector may be configured to compare the second value with the second reference value when the first value is greater than the first reference value.

The reflected light region detector may be configured to determine that the estimated reflected light region is the final polyp region, if the first value is equal to or less than the first reference value.

The reflected light region detector may be configured to determine that the estimated reflected light region as the reflected light region, if the second value is equal to or less than the second reference value.

The reflected light region detector may be configured to determine that the estimated reflected light region is the final polyp region, if the second value is equal to or less than the second reference value.

The display unit may be configured to display a movement trace of the final polyp region when the final polyp region is the same as a previously detected polyp region.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the exemplary embodiments. Expressions such as "at least one of," when preceding a list of elements, modify the entire list of elements and do not modify the individual elements of the list.

The terms used in this specification are those general terms currently widely used in the art in consideration of functions in regard to the exemplary embodiments, but the terms may vary according to the intention of those of ordinary skill in the art, precedents, or new technology in the art. Also, specified terms may be selected by the Applicant, and in this case, the detailed meaning thereof will be described in the detailed description of the exemplary embodiments. Thus, the terms used in the specification should be understood not as simple names but based on the meaning of the terms and the overall description of the exemplary embodiments.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

Throughout the specification, an "image" may refer to an image of an object obtained using an endoscope. Furthermore, in the present specification, "object" may include a person or an animal, or a part of a person or an animal. For example, the object may include the liver, the heart, the womb, the brain, a breast, the abdomen, or a blood vessel. Furthermore, the "object" may include a phantom. The "phantom" may refer to a material having a volume that is approximately the intensity and effective atomic number of a living thing, and may include a sphere phantom having a property similar to a human body. In particular, the object may be an organ or the inside of a body cavity.

In addition, the image may be implemented in various ways. For example, the image may be a black and white image or a color image. In addition, according to an exemplary embodiment, the image may be a two-dimensional (2D) image or a three-dimensional (3D) image.

Furthermore, in the present specification, a "user" may refer to a medical professional, such as a medical doctor, a nurse, a medical laboratory technologist, a medical imaging professional, or an engineer who repairs medical apparatuses, without being limited thereto.

Figure 1:
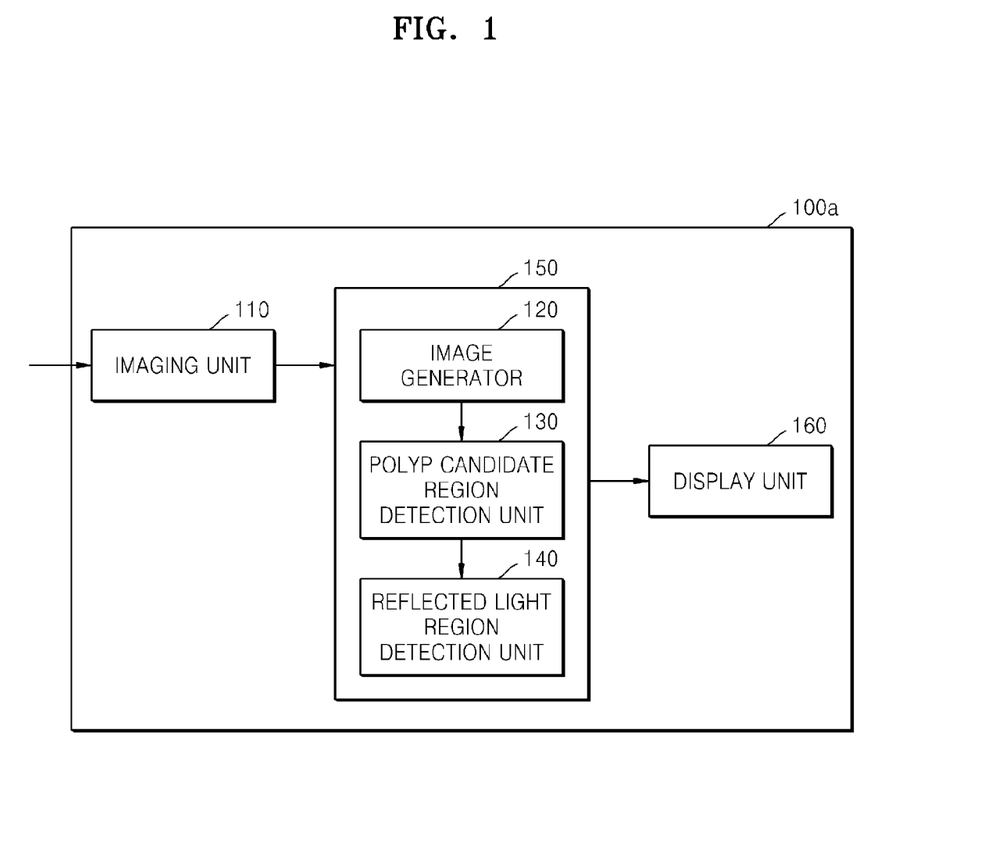
FIG. 1 is a block diagram of a polyp detection apparatus according to an exemplary embodiment.

FIG. 1 is a block diagram of a polyp detection apparatus 100a according to an exemplary embodiment.

Referring to FIG. 1, the polyp detection apparatus 100a includes an imaging unit 110 (e.g., imager), an image processor 150, and a display unit 160 (e.g., display). In addition, the image processor 150 may include an image generator 120, a polyp candidate region detection unit 130 (e.g., polyp candidate region detector), and a reflected light region detection unit 140 (e.g., reflected light region detector).

The imaging unit 110 may acquire an image of an object and transmit an image signal to the image processor 150.

The image generator 120 may generate an image based on the image signal received from the imaging unit 110. The image may be an endoscopic image in black and white or a color image.

The image generator 120 according to an exemplary embodiment may generate a 3D image via a volume rendering process of volume data and may mark a variety of additional information on an image as texts or graphics. The generated image may be stored in a storage unit.

In addition, the image generator 120 may perform a contrast enhancement technique, a deblurring technique, and the like with respect to the generated image, thereby improving image quality.

The polyp candidate region detection unit 130 may detect a polyp candidate region based on the generated image. The polyp candidate region detection unit 130 determines whether the generated image includes feature information of polyps by scanning the generated image, thereby detecting the polyp candidate region.

For example, it may be determined whether the generated image includes feature information of polyps by segmenting the generated image into a plurality of regions, and sequentially comparing the segmented regions with feature information of polyps. In this regard, feature information of polyps may be information indicating shapes or sizes of polyps, or pixel values with respect to polyps.

In addition, the feature information of polyps may be information stored in a database (DB) of the polyp detection apparatus 100a and may be updated continuously.

The reflected light region detection unit 140 may detect a reflected light region by performing an examination of the detected polyp candidate regions. That is, it may be determined whether the detected polyp candidate region is a reflected light region.

For example, the reflected light region detection unit 140 may perform a two-stage examination to detect the reflected light region.

A first stage examination may be performed based on the number of pixels of the detected polyp candidate region and the number of pixels of a region estimated as a reflected light region (estimated reflected light region), and a second stage examination may be performed based on an area of the detected polyp candidate region and an area of the estimated reflected light region.

The reflected light region detection unit 140 may convert an image of the polyp candidate region into a binary image based on pixel values of pixels included in the polyp candidate region.

For example, among red (R), green (G), and blue (B) sub-pixels included in the polyp candidate region, when a sub-pixel value of a B sub-pixel is a preset value or greater, the reflected light region detection unit 140 may set a pixel value of a pixel including the B sub-pixel as a first value.

On the other hand, when the sub-pixel value of the B sub-pixel is less than the preset value, the reflected light region detection unit 140 may set the pixel value of the pixel including the B sub-pixel as a second value. Accordingly, the reflected light region detection unit 140 may convert the image of the polyp candidate region into a binary image having the first value or second value as the pixel value.

However, a method of converting the image of the polyp candidate region into the binary image is not limited by the aforementioned method. The conversion may be performed based on the total sub-pixel values of the R, G, and B sub-pixels, or a respective mean value or minimum value of the sub-pixel values of the R, G, and B sub-pixels.

The reflected light region detection unit 140 may calculate a number Pp of pixels included in the polyp candidate region and a number Ps of pixels of the estimated reflected light region included in the polyp candidate region.

According to an exemplary embodiment, the reflected light region detection unit 140 determines a region having the first value as the pixel value, as an estimated reflected light region in the binary image, and calculates the number of pixels having the first value as the pixel value.

The reflected light region detection unit 140 may determine whether a value Ps/Pp obtained by dividing the number of pixels of the estimated reflected light region by the number of pixels of the polyp candidate region is greater than a preset first reference value.

In this regard, the reflected light region detection unit 140 may determine that the region is not a reflected light region, but a polyp region, when the value Ps/Pp of the estimated reflected light region is equal to or less than the first reference value.

On the other hand, when the value Ps/Pp of the estimated reflected light region is greater than the first reference value, the second stage examination may be performed with respect to the estimated reflected light region.

The reflected light region detection unit 140 may perform an opening calculation with respect to the estimated reflected light region. When the opening calculation is performed with respect to the estimated reflected light region, estimated reflected light regions having smaller areas are removed, and main estimated reflected light regions may be noticed.

Also, the reflected light region detection unit 140 may calculate an area Ap of the polyp candidate region and an area As of the estimated reflected light region, and may determine whether a value As/Ap obtained by dividing the area of the estimated reflected light region by the area of the polyp candidate region is greater than a preset second reference value.

In this regard, the reflected light region detection unit 140 may determine that the region is not a reflected light region, but a polyp region, when the As/Ap of the estimated reflected light region is equal to or less than the second reference value.

On the other hand, when the value As/Ap of the estimated reflected light region is greater than the second reference value, the estimated reflected light region may be determined as a reflected light region.

The image processor 150 may exclude regions determined as the reflected light regions from the polyp candidate region, and the display unit 160 may display a final polyp region from which regions determined as the reflected light regions are removed.

The display unit 160 displays and outputs an endoscopic image generated by the image processor 150. The display unit 160 may also display and output a variety of information processed by the polyp detection apparatus 100a in addition to the endoscopic image on a screen via a graphic user interface (GUI). According to an exemplary embodiment, the polyp detection apparatus 100a may include two or more display units according to configurations thereof.

The display unit 160 may include at least one display selected from the group consisting of liquid crystal displays, thin film transistor-liquid crystal displays, organic light-emitting diodes, flexible displays, 3D displays, and electrophoretic displays.

In addition, when the display unit 160 and a user input unit constitute a touch screen in a layered structure, the display unit 160 may also be used as an input device to which information is input via a touch by a user as well as an output device.

In addition, the display unit 160 may display identification, detection time, movement trace, and the like with respect to the detected polyps, and may also display various measurement menus with respect to the detected polyps.

Figure 2:
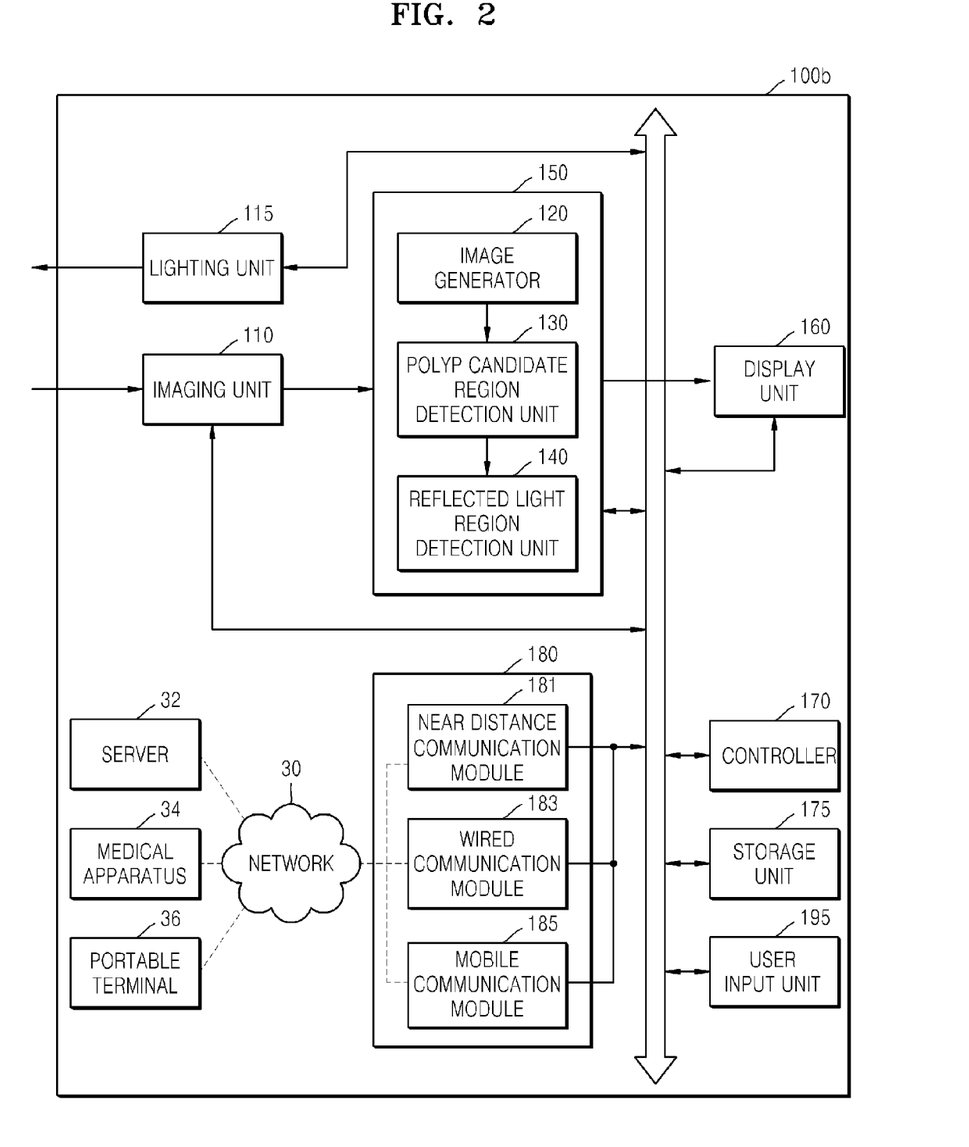
FIG. 2 is a block diagram of a polyp detection apparatus according to an exemplary embodiment.

FIG. 2 is a block diagram of a polyp detection apparatus 100b according to an exemplary embodiment.

Referring to FIG. 2, the polyp detection apparatus 100b includes a lighting unit 115, an imaging unit 110, an image processor 150, a display unit 160, a communication unit 180, a storage unit 175, a user input unit 195, and a controller 170, and these constituent elements may be connected to one another via a bus.

The imaging unit 110, the image processor 150, and the display unit 160 of FIG. 2 may be the same as the imaging unit 110, the image processor 150, and the display unit 160 of FIG. 1, and thus detailed descriptions thereof will not be repeated herein.

The lighting unit 115 may emit light to illuminate a target region, such as the inside of a body cavity, for an endoscopic image.

The communication unit 180 communicates with an external device or a server in a state of being connected to a network 30 in a wired or wireless manner. The communication unit 180 may transmit and/or receive data to and/or from a server of a hospital or a medical apparatus in the hospital connected via a Picture Archiving and Communication System (PACS). In addition, the communication unit 180 may perform data communication via Digital Imaging and Communications in Medicine (DICOM).

The communication unit 180 may perform transmission and reception of data related to diagnosis of an object such as an endoscopic image of the object and endoscopic data via the network 30, and may also perform transmission and reception of medical images acquired by another medical apparatus such as an endoscope, an ultrasonic imaging apparatus, a CT scanner, an MRI apparatus, and an X-ray apparatus. Moreover, the communication unit 180 may receive information related to a medical history or treatment schedule of an object (e.g., a patient) from the server to diagnose a disease of the object. Furthermore, the communication unit 180 may perform data communication with a portable terminal of a doctor or a patient, in addition to the server or medical apparatus of the hospital.

The communication unit 180 may be connected to the network 30 via wires or wirelessly to transmit and/or receive data to and/or from a server 32, a medical apparatus 34, or a portable terminal 36. The communication unit 180 may include one or more elements enabling communication with external devices, for example, a near distance communication module 181, a wired communication module 183, and a mobile communication module 185.

The near distance communication module 181 is a module for communicating with a device located within a predetermined distance. The near distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like, without being limited thereto.

The wired communication module 183 is a module for communications by using an electric signal or an optical signal, and the wired communication technology may be implemented as a wired communication technology using a pair cable, a coaxial cable, an optical fiber cable, and an Ethernet cable.

The mobile communication module 185 may transmit and/or receive a wireless signal to and/or from at least one of a base station, an external terminal, and a server in a mobile communication network. According to an exemplary embodiment, the wireless signal may be a voice call signal, a video call signal, or various types of data according to transmission of text and/or multimedia messages.

The storage unit 175 stores a variety of information processed by the polyp detection apparatus 100b. For example, the storage unit 175 may store medical data related to a diagnosis of a disease of the object such as input and output image data, feature information data of polyps, and data related to detected polyps, and may also store algorithms or programs to be performed in the polyp detection apparatus 100b.

The storage unit 175 may be implemented by using a storage medium such as a flash memory, a hard disk drive, and an electrically erasable programmable read-only memory (EEPROM). In addition, the polyp detection apparatus 100b may operate a web storage providing data-storing functions of the storage unit 175 on the World Wide Web or a cloud server.

The user input unit 195 generates input data input by a user to control an operation of the polyp detection apparatus 100b. The user input unit 195 may include a hardware component such as a key pad, a mouse, a touch pad, a trackball, and a jog switch, without being limited thereto. The user input unit 195 may further include various components such as an electrocardiogram (ECG) module, a respiratory measurement module, a voice recognition sensor, a gesture recognition sensor, a fingerprint recognition sensor, an iris recognition sensor, a depth sensor, and a distance sensor.

In particular, the user input unit 195 may include a touch screen in which the touch pad and the display unit 160 constitute a layered structure.

In this regard, the polyp detection apparatus 100b according to an exemplary embodiment may display an endoscopic image in a predetermined mode and a control panel with regard to the endoscopic image on the touch screen. In addition, the polyp detection apparatus 100b senses a touch gesture of the user with respect to the endoscopic image via the touch screen.

The controller 170 controls an overall operation of the polyp detection apparatus 100b. That is, the controller 170 may control operations of the lighting unit 115, the imaging unit 110, the image processor 150, the communication unit 180, the storage unit 175, and the user input unit 195.

Some or all of the lighting unit 115, the imaging unit 110, the image processor 150, the communication unit 180, the storage unit 175, the user input unit 195, and the controller 170 may operate by a software module, without being limited thereto. Some of these components may operate by hardware. In addition, at least one of the image processor 150 and the communication unit 180 may be included in the controller 170, without being limited thereto.

According to an exemplary embodiment, the polyp detection apparatuses 100a and 100b of FIGS. 1 and 2 may be implemented not only as a cart type apparatus but also as a portable type apparatus. Examples of a portable ultrasonic diagnostic apparatus may include a picture archiving and communication system (PACS) viewer, a smart phone, a laptop computer, a personal digital assistant (PDA), and a tablet PC, without being limited thereto.

In addition, the block diagrams of the polyp detection apparatuses 100a and 100b of FIGS. 1 and 2 are block diagrams according to an exemplary embodiment. Constituent elements of the block diagrams may be integrated, added, or omitted according to performance of ultrasonic diagnostic apparatuses. That is, two or more elements may be integrated into one element, or one element may be separated into two or more elements. In addition, functions performed by each block are provided for descriptive convenience of the exemplary embodiments, and details related to the operations or the devices are not intended to limit the scope of the exemplary embodiments.

Figure 3:
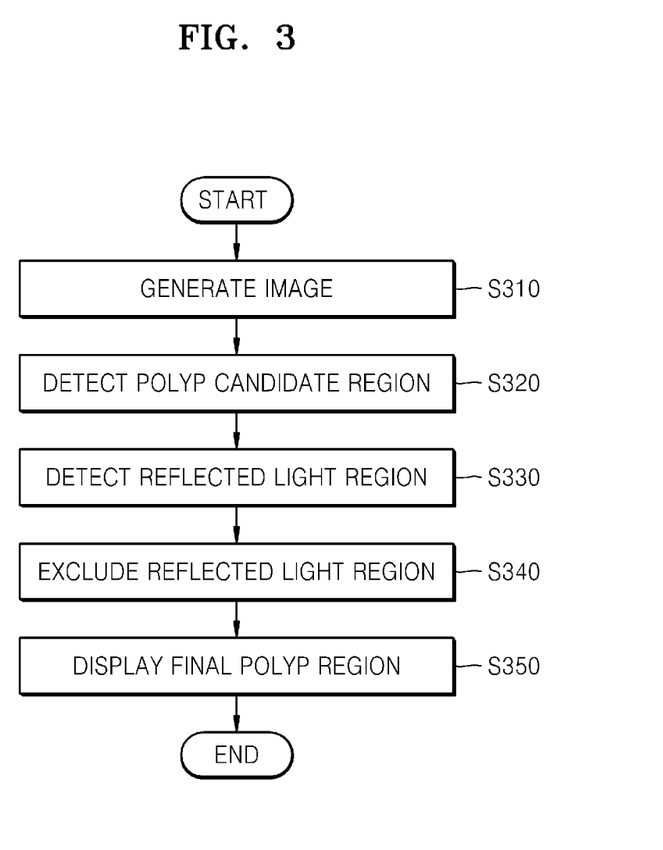
FIG. 3 is a flowchart for describing a method of operating a polyp detection apparatus according to an exemplary embodiment.

FIG. 3 is a flowchart for describing a method of operating a polyp detection apparatus according to an exemplary embodiment.

Referring to FIG. 3, the polyp detection apparatuses 100a and 100b may generate an image at operation S310. In this regard, the image may be an endoscopic image. For example, the image may be an image acquired by illuminating a target region for imaging, such as the inside of a body cavity, and imaging the target region by using an endoscope.

In addition, the polyp detection apparatuses 100a and 100b may perform a contrast enhancement technique, a deblurring technique, and the like with respect to the generated image, thereby improving image quality.

According to an exemplary embodiment, the polyp detection apparatuses 100a and 100b may detect a polyp candidate region based on the generated image at operation S320.

The polyp detection apparatuses 100a and 100b determine whether the generated image includes feature information of polyps by scanning the generated image, thereby detecting the polyp candidate region.

For example, it may be determined whether the generated image includes feature information of polyps by segmenting the generated image into a plurality of regions, and sequentially comparing the segmented regions with the feature information of polyps. In this regard, feature information of polyps may be information indicating shapes or sizes of polyps, or pixel values with respect to polyps.

In addition, the feature information of polyps may be information stored in a database (DB) of the polyp detection apparatuses 100a and 100b and may be updated continuously.

Figure 6:
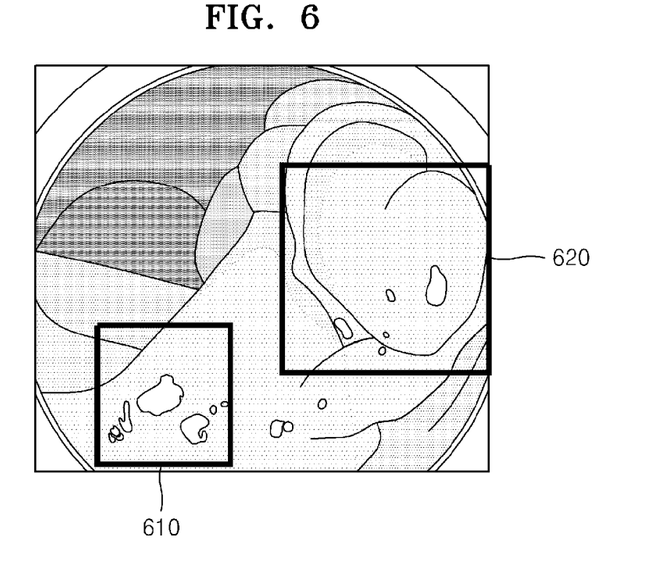
FIGS. 6, 7A, 7B, 8A, 8B, 9A, 9B, 10 and 11 are diagrams for describing the method of FIGS. 3 to 5.

FIG. 6 is a diagram of a screen displaying a detection result of a polyp candidate region based on the method described above. Referring to FIG. 6, the detected polyp candidate region may be marked as a rectangular box. However, the method of marking the poly candidate region is not limited thereto, and the polyp candidate region may also be marked by using a circular or polygonal shape, or other types of shapes.

As illustrated in FIG. 6, a plurality of polyp candidate regions may be detected and may be indicated as a first polyp candidate region 610 and a second polyp candidate region 620.

According to an exemplary embodiment, the polyp detection apparatuses 100a and 100b examine the detected polyp candidate region to detect reflected light regions at operation S330. That is, it may be determined whether the detected polyp candidate region is a reflected light region.

For example, the polyp detection apparatuses 100a and 100b may perform a two-stage examination to detect the reflected light region.

Figure 4:
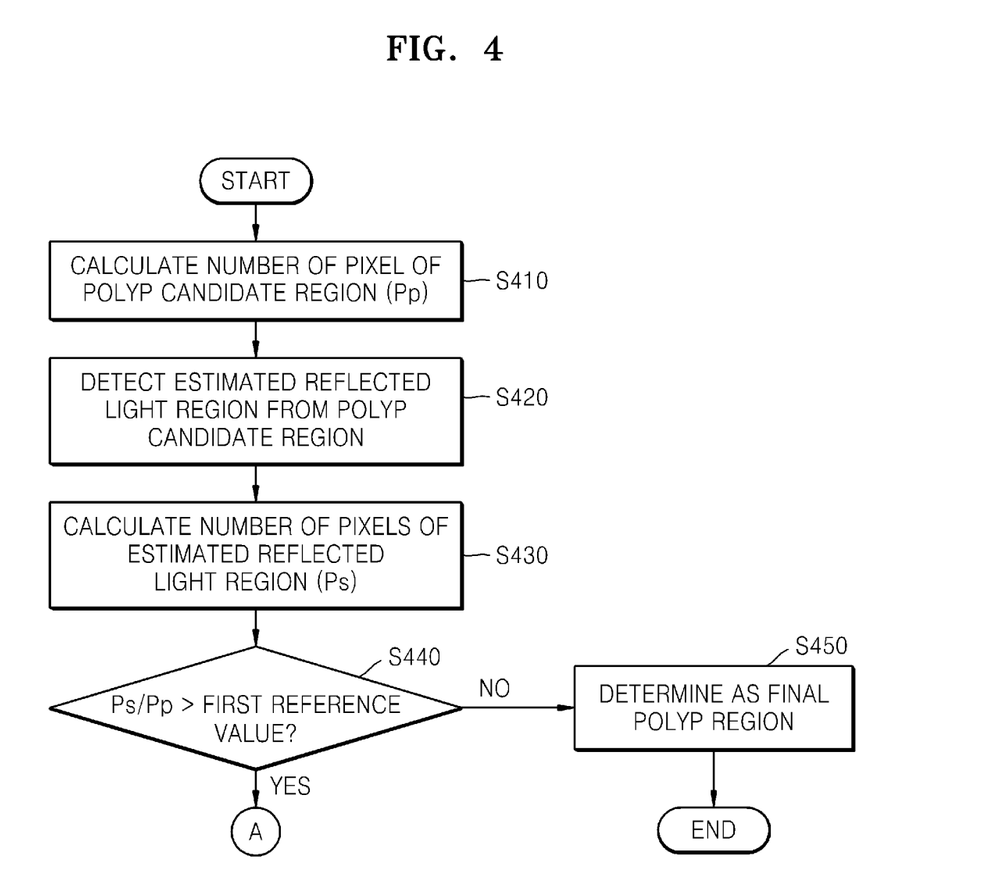
FIGS. 4 and 5 are flowcharts for describing operation 330 (S330) of FIG. 3 in more detail.
Figure 5:
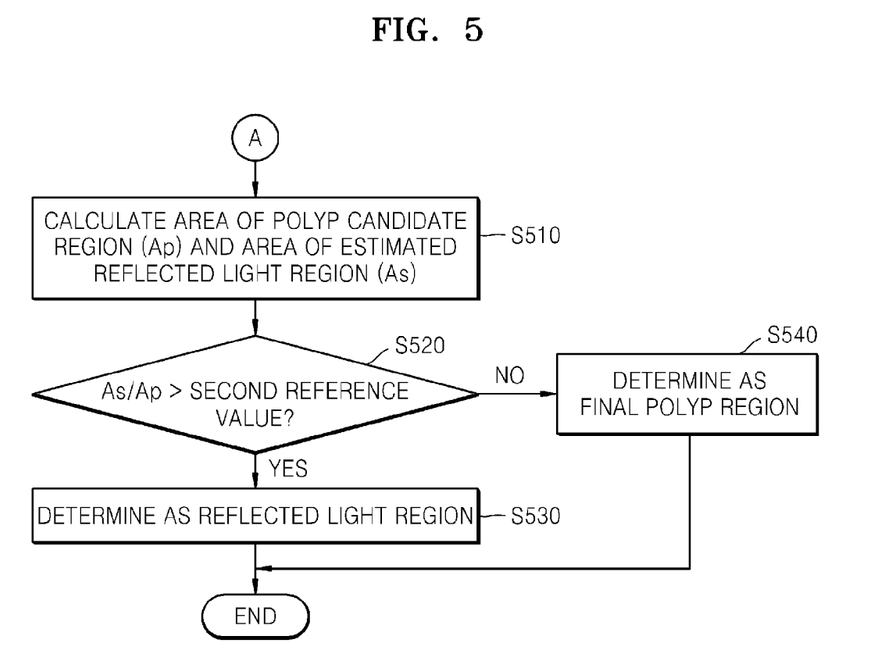

FIGS. 4 and 5 are flowcharts for describing operation 330 (S330) of FIG. 3 in more detail. FIG. 4 is a flowchart for describing a first stage examination to detect reflected light regions, and FIG. 5 is a flowchart for describing a second stage examination to detect the reflected light regions.

The first stage examination may be performed based on a number of pixels of a detected polyp candidate region and a number of pixels of a region estimated as a reflected light region (an estimated reflected light region), and the second stage examination may be performed based on an area of the detected polyp candidate region and an area of the estimated reflected light region.

Referring to FIG. 4, the polyp detection apparatuses 100a and 100b may calculate the number Pp of pixels included in the polyp candidate region at operation S410.

In addition, the polyp detection apparatuses 100a and 100b may detect regions estimated as reflected light regions (estimated reflected light regions) in the detected polyp candidate region at operation S420.

In this regard, the polyp detection apparatuses 100a and 100b may convert an image of the polyp candidate region into a binary image based on the pixel value of the pixels included in the polyp candidate region, and detect the estimated reflected light region based on the binary image.

For example, among red (R), green (G), and blue (B) sub-pixels included in the polyp candidate region, when a sub-pixel value of a B sub-pixel is a preset value or greater, the polyp detection apparatuses 100a and 100b 140 may set a pixel value of a pixel including the B sub-pixel as a first value.

On the other hand, when the sub-pixel value of the B sub-pixel is less than the preset value, the pixel value of the pixel including the B sub-pixel may be set as a second value. Accordingly, the image of the polyp candidate region may be converted into a binary image having the first value or second value as the pixel value.

Figure 7A:
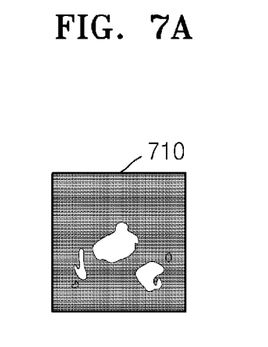
Figure 7B:
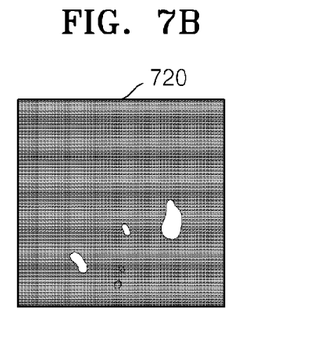

FIGS. 7A and 7B are diagrams illustrating a converted binary image based on the method described above.

For example, by examining a sub-pixel value of a B sub-pixel of a pixel of the first polyp candidate region 610 and the second polyp candidate region 620 of FIG. 6, the polyp detection apparatuses 100a and 100b may set the pixel to have the first value when the B sub-pixel value is a preset value or greater and may set the pixel to have the second value when the B sub-pixel value is less than the preset value.

Accordingly, as illustrated in FIGS. 7A and 7B, the first polyp candidate region 610 and the second polyp candidate region 620 of the binary images 710 and 720 may be expressed by using white corresponding to the first value and black corresponding to the second value.

However, a method of converting the image of the polyp candidate region into the binary image is not limited by the aforementioned method. The conversion may be performed based on the total sub-pixel values of the R, G, and B sub-pixels, or based on respective mean values or minimum values of the R, G, and B sub-pixel values, or in other ways known to those skilled in the art.

The polyp detection apparatuses 100a and 100b may detect the region having the first value as the pixel value in the converted binary image as the estimated reflected light region.

Meanwhile, referring back to FIG. 4, the polyp detection apparatuses 100a and 100b may calculate the number Ps of pixels of the estimated reflected light region in the converted binary image at operation S430.

For example, when the region having the first value as the pixel value in the binary image is determined as the estimated reflected light region, the polyp detection apparatuses 100a and 100b may calculate the number of pixels having the first value as the pixel value.

The polyp detection apparatuses 100a and 100b may determine whether a value Ps/Pp obtained by dividing the number of pixels of the estimated reflected light region by the number of pixels of the polyp candidate region is greater than a preset first reference value at operation S440.

In this regard, the polyp detection apparatuses 100a and 100b may determine that the region is not a reflected light region, but a final polyp region, when the value Ps/Pp is equal to or less than the first reference value at operation S450.

On the other hand, when the value Ps/Pp is greater than the first reference value, the region is determined as the estimated reflected light region, and the second stage examination may be performed with respect to the region.

While performing the second stage examination, the polyp detection apparatuses 100a and 100b may perform an opening calculation with respect to the estimated reflected light region.

Figures 8A, 8B:
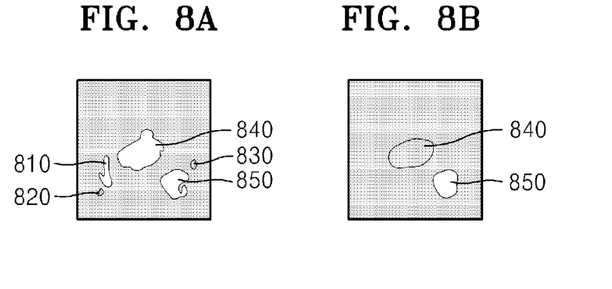

Referring to FIGS. 8A and 8B, FIG. 8A illustrates an estimated reflected light region before performing the opening calculation, and FIG. 8B illustrates the estimated reflected light region after performing the opening calculation.

When the opening calculation is performed with respect to the estimated reflected light region, estimated reflected light regions having smaller areas are removed, and main estimated reflected light regions may be noticed.

For example, when the opening calculation is performed, estimated reflected light regions 810, 820, and 830 having smaller areas in FIG. 8A are removed and are not illustrated in FIG. 8B, and main estimated reflected light regions 840 and 850 may be illustrated to be wider in FIG. 8B.

Referring back to FIG. 5, the polyp detection apparatuses 100a and 100b may calculate an area Ap of the polyp candidate region and an area As of the estimated reflected light region, and may determine whether a value As/Ap obtained by dividing the area of the estimated reflected light region by the area of the polyp candidate region is greater than a second reference value.

In this regard, the polyp detection apparatuses 100a and 100b may determine that the region is not a reflected light region, but a final polyp region, when the value As/Ap is equal to or less than the second reference value at operation S540.

On the other hand, when the value As/Ap is greater than the second reference value, the region may be determined as a reflected light region at operation S530.

Referring back to FIG. 3, the polyp detection apparatuses 100a and 100b may exclude the detected reflected light region from the polyp candidate region, and display a final polyp region at operation S350.

Figure 9A:
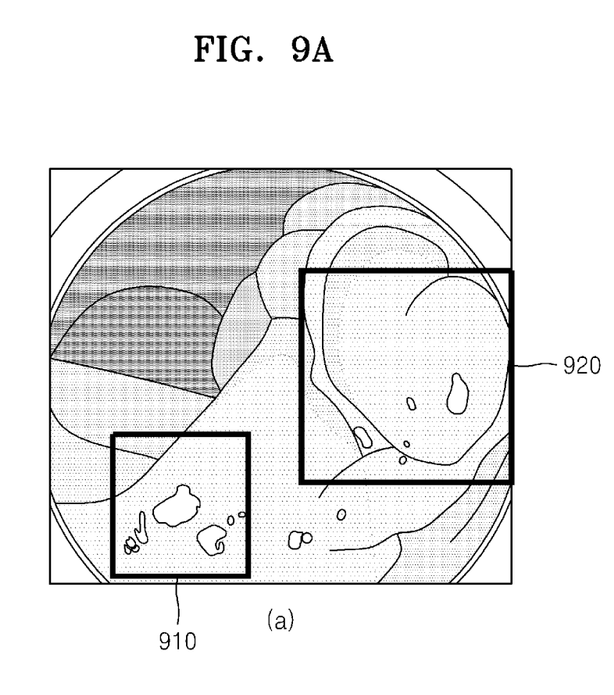
Figure 9B:
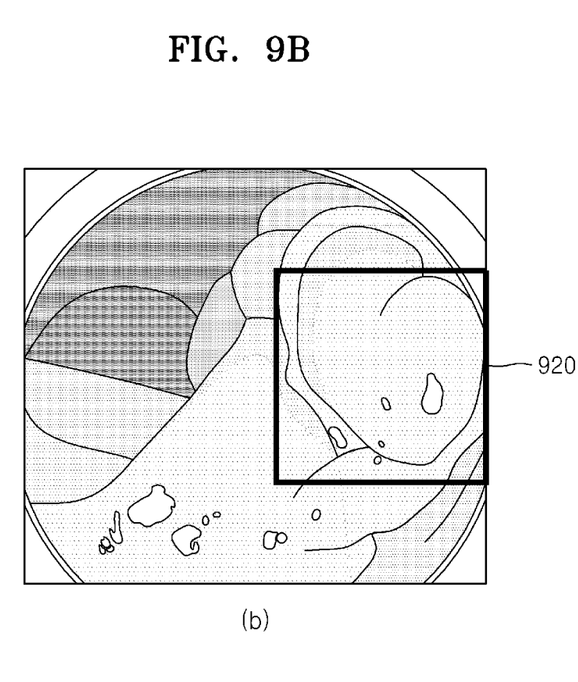

For example, referring to FIGS. 9A and 9B, an initially detected polyp candidate region may include a first polyp candidate region 910 and a second polyp candidate region 920 as illustrated in FIG. 9A. The first polyp candidate region 910 may be determined as a reflected light region in the first stage and second stage examinations and may not be displayed as a final polyp region as illustrated in FIG. 9B.

Figure 10:
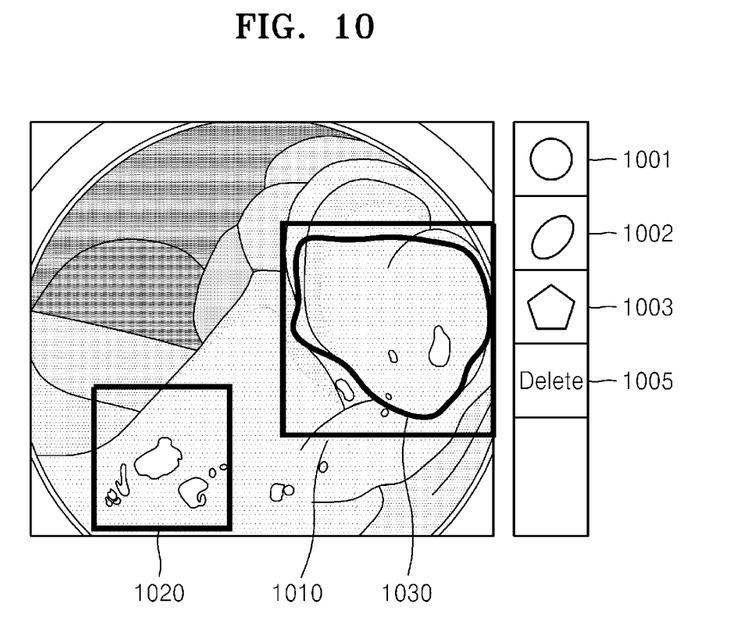
Figure 11:
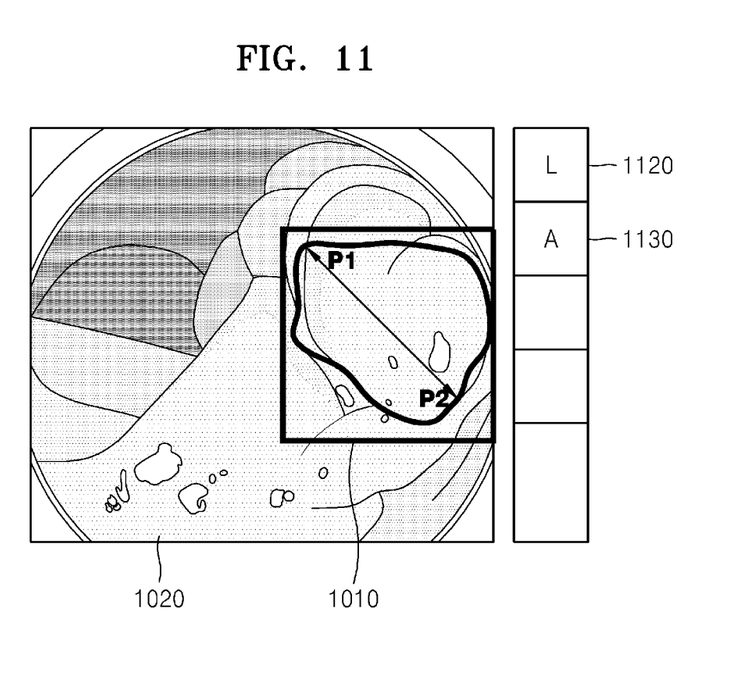

FIGS. 10 and 11 are diagrams illustrating polyps detected according to an exemplary embodiment and displayed on a display unit.

When the polyp region is detected, the polyp detection apparatuses 100a and 100b may display the detected polyp region on the display unit 160.

In this regard, the polyp detection apparatuses 100a and 100b may detect polyps by using the method as described above with reference to FIGS. 3 to 5, and may display the detected polyps by using various methods.

For example, as illustrated in FIG. 10, the polyp detection apparatuses 100a and 100b may detect and display borderlines 1030 of polyps. Alternatively, the detected polyps may be marked by using a selected object among a circular object 1001, an oval object 1002, and a polygonal object 1003 in response to a user input to select one of a plurality of objects.

According to an exemplary embodiment, the polyp detection apparatuses 100a and 100b may exclude some polyp regions from the detected and displayed polyp regions.

The polyp detection apparatuses 100a and 100b select at least one of the plurality of polyp regions 1010 and 1020 which are detected as final polyp regions and marked by using indicators (e.g., rectangular boxes) in the display unit 160 and may allow the selected polyp region not to be marked by using the rectangular box upon receiving an input to select a polyp region excluding button 1005.

For example, the user may select the second polyp region 1020 between the first polyp region 1010 and the second polyp regions 1020 marked by using the rectangular boxes in FIG. 10. When the user selects the polyp region excluding button 1005, the second polyp region 1020 is not marked with the rectangular box as illustrated in FIG. 11.

According to an exemplary embodiment, the polyp detection apparatuses 100a and 100b may perform various measurements with respect to the displayed polyp regions.

For example, as illustrated in FIG. 11, the polyp detection apparatuses 100a and 100b may display a distance measurement menu 1120, an area measurement menu 1130, and the like on the display unit 160. When the user selects the distance measurement menu 1120 and selects two points P1 and P2 by using an input device such as a mouse or a touch tool, the polyp detection apparatuses 100a and 100b may measure a distance between the two points P1 and P2 and display the distance. Alternatively, when the user selects the distance measurement menu 1120, the polyp detection apparatuses 100a and 100b may automatically measure and display a greatest length and a smallest length of a polyp.

Alternatively, when the user selects the area measurement menu 1130 and selects a region of a polyp displayed on the display unit 160 by using an input device such as a mouse or a touch tool, the polyp detection apparatuses 100a and 100b may measure and display the area of the selected region. Alternatively, when the user selects the area measurement menu 1130, the area of the polyp may be automatically measured and displayed.

FIG. 11 exemplarily illustrates a distance measurement menu and an area measurement menu. However, the exemplary embodiments are not limited thereto, and various other numerical values with respect to the displayed polyp may also be measured and displayed.

Figure 12:
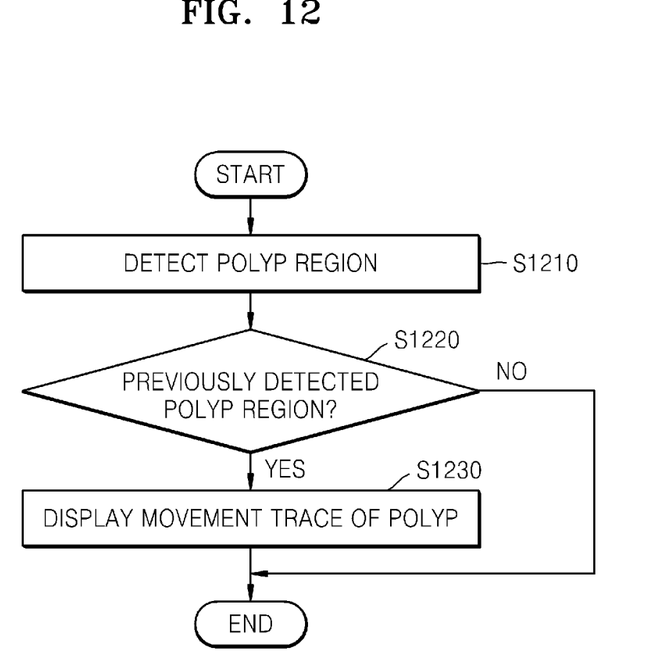
FIG. 12 is a flowchart for describing a method of operating a polyp detection apparatus according to an exemplary embodiment n.

FIG. 12 is a flowchart for describing a method of operating a polyp detection apparatus according to an exemplary embodiment.

Referring to FIG. 12, when polyp regions are detected at operation S1210, the polyp detection apparatuses 100a and 100b may determine whether the detected polyp regions are the same as previously detected polyp regions at operation S1220.

When a polyp is detected, the polyp detection apparatuses 100a and 100b may assign an identification (ID) to the detected polyp. In addition, information regarding the detected polyp may be stored in a storage unit as a database.

Although not shown herein, a time when the polyp is detected may also be displayed together with the polyp or stored in a database to be used as a reference for a subsequent diagnosis of the same polyp.

Accordingly, when the polyp is detected, the polyp detection apparatuses 100a and 100b may search the database to determine whether the detected polyp is the same as a previously detected polyp. In this regard, it may be determined whether the detected polyp is the same as the previously detected polyp by comparing information regarding the previously detected polyp with information regarding the newly detected polyp.

Upon a determination that the newly detected polyp is different from the previously detected polyp, an ID may be assigned to the newly detected poly, and information regarding the newly detected polyp and the ID may be stored in the database.

On other hand, when the newly detected polyp is the same as the previously detected polyp, a movement trace of the polyp may be calculated and displayed at operation S1230.

For example, the polyp detection apparatuses 100a and 100b may calculate a movement trace of the polyp in a current frame based on the location of a previous frame and may display the result. In this regard, the polyp detection apparatuses 100a and 100b may calculate the movement trace by using a Kalman filtering technique based on the fact that a size or location of a polyp is not rapidly changed compared to those of a previous frame. However, the exemplary embodiments are not limited thereto, and various other calculation methods may also be used. In addition, the movement trace may be marked as dashed lines as illustrated in FIG. 13A.

Figure 13A:
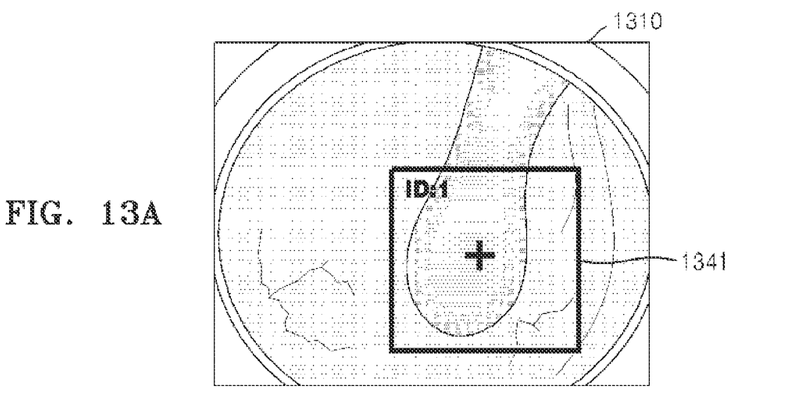
FIGS. 13A, 13B and 13C are diagrams for describing the method of FIG. 12.

For example, the polyp detection apparatuses 100a and 100b may detect a first polyp 1341 in a first frame 1310, display the first polyp 1341 on a screen, and assign a first ID (ID:1) to the first polyp 1341 as illustrated in FIG. 13A.

Figure 13B:
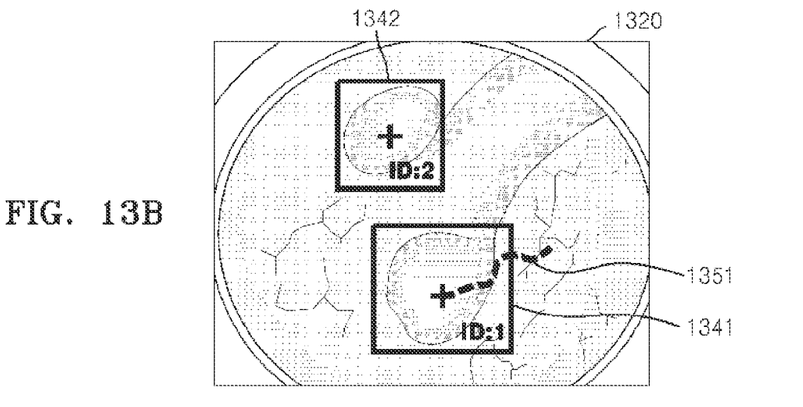

In addition, the polyp detection apparatuses 100a and 100b may detect the first polyp 1341 and a second polyp 1342 in a second frame 1320, mark a movement trace 1351 of the first polyp 1341, which is the same as that previously detected in a previous frame (first frame 1310), assign a second ID (ID:2) to the newly detected second polyp 1342, and display the results on the screen as illustrated in FIG. 13B.

Figure 13C:
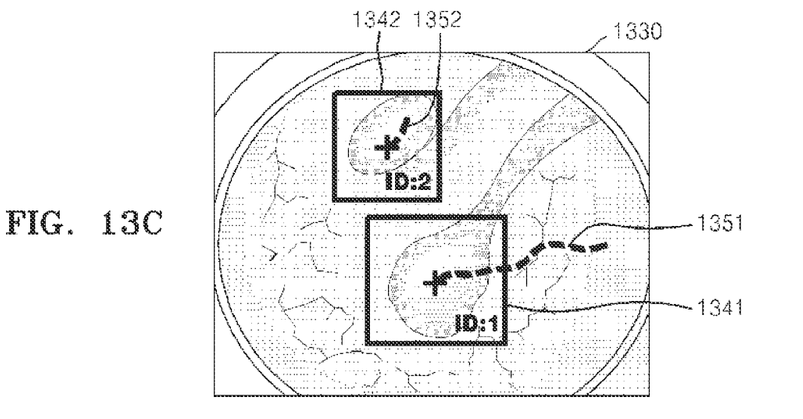

In the same manner, since the first and second polyps 1341 and 1342 detected in a third frame 1330 are the same as those previously detected in the previous frame (second frame 1320), the polyp detection apparatuses 100a and 100b do not assign new IDs to the detected first and second polyps 1341 and 1342, but calculate and display the movement traces 1351 and 1352 as illustrated in FIG. 13C.

As described above, since the polyp detection apparatus shows the movement of the polyp, the user may easily determine the movement path of the polyp, although the frames are different, thereby efficiently tracing the polyp.

In addition, ultrasonic diagnostic apparatuses and operating methods thereof according to exemplary embodiments can also be implemented through computer readable code or instructions stored in or on a medium, e.g., a computer readable medium, to control at least one processing element to implement any above described exemplary embodiment. The medium can correspond to any medium or media permitting the storage and/or transmission of the computer readable code.

The computer readable code can be recorded or transferred on a medium in a variety of ways, with examples of the medium including recording media, such as magnetic storage media (e.g., ROM, floppy disks, hard disks, etc.), optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer readable code is stored or transferred and executed in a distributed fashion. Furthermore, the processing element could include a processor or a computer processor, and processing elements may be distributed and/or included in a single device.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the exemplary embodiments as defined by the following claims.

What is claimed is:

1. A method of operating a polyp detection apparatus, the method comprising:
generating an image of an object;
detecting polyp candidate regions including a reflected light region, based on the generated image;
determining whether each of the polyp candidate regions is the reflected light region based on a number of pixels of each of the polyp candidate regions and a number of pixels of an estimated reflected light region included in each of the polyp candidate regions; and
displaying a final polyp region by excluding the reflected light region from the polyp candidate regions.

2. The method of claim 1, wherein the detecting of the polyp candidate regions is performed based on feature information of polyps.

3. The method of claim 1, further comprising converting the generated image into a binary image,
wherein the determining whether each of the polyp candidate regions is the reflected light region is performed based on the binary image.

4. The method of claim 1, wherein the determining whether each of the polyp candidate regions is the reflected light region is performed based on an area of each of the polyp candidate regions and an area of the estimated reflected light region included in each of the polyp candidate regions.

5. The method of claim 1, wherein the determining whether each of the polyp candidate regions is the reflected light region comprises selectively performing a first stage and a second stage,
wherein the first stage comprises comparing a first value with a first reference value, the first value being obtained by dividing the number of pixels of the estimated reflected light region included in each of the polyp candidate regions by the number of pixels of each of the polyp candidate regions, and
the second stage comprises comparing a second value with a second reference value, the second value being obtained by dividing an area of the estimated reflected light region included in each of the polyp candidate region by an area of each of the polyp candidate regions.

6. The method of claim 5, wherein the determining whether each of the polyp candidate regions is the reflected light region comprises performing the second stage when the first value is greater than the first reference value in the first stage.

7. The method of claim 5, wherein the determining whether each of the polyp candidate regions is the reflected light region comprises determining each of the polyp candidate regions to be the final polyp region if the first value is equal to or less than the first reference value in the first stage.

8. The method of claim 5, wherein the determining whether each of the polyp candidate regions is the reflected light region comprises determining each of the polyp candidate regions to be the reflected light region if the second value is greater than the second reference value in the second stage.

9. The method of claim 5, wherein the determining whether each of the polyp candidate regions is the reflected light region comprises determining each of the polyp candidate regions to be the final polyp region if the second value is equal to or less than the second reference value in the second stage.

10. The method of claim 1, further comprising comparing the final polyp region with a previously detected polyp region,
wherein the displaying of the final polyp region comprises displaying a movement trace of the final polyp region when the final polyp region is the same as the previously detected polyp region.

11. A polyp detection apparatus comprising:
an imager configured to image an object and thereby generate an image signal;
an image processor configured to generate an image based on the image signal received from the imager, detect polyp candidate regions based on the generated image, and determine whether each of the polyp candidate regions is a reflected light region based on a number of pixels of each of the polyp candidate regions and a number of pixels of an estimated reflected light region included in each of the polyp candidate regions; and
a display configured to display a final polyp region by excluding the reflected light region from the polyp candidate regions.

12. The polyp detection apparatus of claim 11, wherein the image processor is configured to detect the polyp candidate regions based on feature information of polyps.

13. The polyp detection apparatus of claim 11, wherein the image processor is configured to convert the generated image into a binary image and determine whether each of the polyp candidate regions is the reflected light region based on the binary image.

14. The polyp detection apparatus of claim 11, wherein the image processor is configured to determine whether each of the polyp candidate regions is the reflected light region based on an area of each of the polyp candidate regions and an area of the estimated reflected light region included in each of the polyp candidate regions.

15. The polyp detection apparatus of claim 11, wherein the image processor is configured to compare a first value with a first reference value, the first value being obtained by dividing the number of pixels of the estimated reflected light region included in each of the polyp candidate regions by the number of pixels of each of the polyp candidate regions, and
compare a second value with a second reference value, the second value being obtained by dividing an area of the estimated reflected light region included in each of the polyp candidate regions by an area of each of the polyp candidate regions.

16. The polyp detection apparatus of claim 15, wherein the image processor is configured to compare the second value with the second reference value when the first value is greater than the first reference value.

17. The polyp detection apparatus of claim 15, wherein the image processor is configured to determine that each of the polyp candidate regions is the final polyp region if the first value is equal to or less than the first reference value.

18. The polyp detection apparatus of claim 15, wherein the image processor is configured to determine that each of the polyp candidate regions is the reflected light region if the second value is greater than the second reference value.

19. The polyp detection apparatus of claim 15, wherein the image processor is configured to determine that each of the polyp candidate regions is the final polyp region if the second value is equal to or less than the second reference value.

20. The polyp detection apparatus of claim 11, wherein the display is configured to display a movement trace of the final polyp region when the final polyp region is the same as a previously detected polyp region.

21. A non-transitory computer-readable recording medium storing a computer-readable program for executing the method of claim 1.

* * * * *